United States Patent
Mo

[19]

[11] Patent Number: 6,014,897
[45] Date of Patent: Jan. 18, 2000

[54] METHOD AND APPARATUS FOR IMPROVING SIDELOBE PERFORMANCE OF SPARSE ARRAY USING HARMONIC IMAGING

[76] Inventor: Larry Y. L. Mo, 1707 Saratoga Rd., Waukesha, Wis. 53186

[21] Appl. No.: 09/145,533

[22] Filed: Sep. 2, 1998

[51] Int. Cl.[7] .............................. G01N 29/00; H04B 1/06
[52] U.S. Cl. .............................. 73/628; 367/135
[58] Field of Search .................. 73/618, 620, 625, 73/627, 628, 631, 632, 633; 128/660.01, 660.04, 660.05, 660.07, 661.03; 367/135, 138

[56] References Cited

U.S. PATENT DOCUMENTS

| | | | |
|---|---|---|---|
| 4,633,883 | 1/1987 | Matsui | 128/660 |
| 5,027,658 | 7/1991 | Anderson | 73/625 |
| 5,050,226 | 9/1991 | Collet-Billon | 382/54 |
| 5,090,412 | 2/1992 | Shimazaki | 128/660.07 |
| 5,186,175 | 2/1993 | Hirama et al. | 128/661.01 |
| 5,235,857 | 8/1993 | Anderson | 73/625 |
| 5,555,534 | 9/1996 | Maslak et al. | 367/135 |
| 5,581,517 | 12/1996 | Gee et al. | 367/138 |
| 5,677,491 | 10/1997 | Ishrak et al. | 73/641 |

FOREIGN PATENT DOCUMENTS

WO 98/20361 5/1998 WIPO.

OTHER PUBLICATIONS

Turnbull and Foster, "Beam steering with pulsed two-dimensional transducer arrays," IEEE Trans. Ultrasonics, Ferroelectrics, and Frequency Control, vol. 18, pp. 320–333 (1991).

Smith et al., "Two-dimensional arrays for medical ultrasound," Ultrasonic Imaging, vol. 14, pp. 213–233 1992).

Primary Examiner—Richard A. Moller
Attorney, Agent, or Firm—Dennis M. Flaherty; Christian G. Cabou; Phyllis Y. Price

[57] ABSTRACT

A method and an apparatus for enhancing the side-lobe performance of a sparse ultrasonic transducer array using harmonic imaging to reduce all beam sidelobe (including grating lobe) levels. Harmonic imaging consists of using the active transducer elements to transmit an ultrasound signal (wideband or narrowband) of center frequency $f_0$ and receive at one or more harmonic frequencies $nf_0$, where $n \geq 2$.

20 Claims, 4 Drawing Sheets

METHOD AND APPARATUS FOR IMPROVING SIDELOBE PERFORMANCE OF SPARSE ARRAY USING HARMONIC IMAGING

FIELD OF THE INVENTION

This invention generally relates to ultrasound imaging of the human anatomy for the purpose of medical diagnosis. In particular, the invention relates to methods for reducing the beam sidelobes and grating lobes of a sparse transducer array.

BACKGROUND OF THE INVENTION

Conventional ultrasound scanners create two-dimensional B-mode images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The frequency shift of backscattered ultrasound waves may be used to measure the velocity of the backscatterers from tissue or blood. The Doppler shift may be displayed using different colors to represent speed and direction of flow. In power Doppler imaging, the power contained in the returned Doppler signal is displayed.

Conventional ultrasound transducers transmit a broadband signal centered at a fundamental frequency $f_0$, which is applied separately to each transducer element making up the transmit aperture by a respective pulser. The pulsers are activated with time delays that produce the desired focusing of the transmit beam at a particular transmit focal position. As the transmit beam propagates through tissue, echoes are created when the ultrasound wave is scattered or reflected off of the boundaries between regions of different density. The transducer array is used to transduce these ultrasound echoes into electrical signals, which are processed to produce an image of the tissue. These ultrasound images are formed from a combination of fundamental and (sub) harmonic signal components, the latter of which are generated in a nonlinear medium such as tissue or a blood stream containing contrast agents.

In certain instances ultrasound images may be improved by suppressing the fundamental and emphasizing the (sub) harmonic (nonlinear) signal components. If the transmitted center frequency is at $f_0$, then tissue/contrast nonlinearities will generate harmonics at $kf_0$, where k is an integer greater than or equal to 2. Also, subharmonics at frequencies $f_0/k$ may be generated by contrast bubble destruction. Imaging of (sub)harmonic signals has been performed by transmitting a narrowband signal at frequency $f_0$ and receiving at a band centered at frequency $2f_0$ (second harmonic) or at frequency $f_0/2$ (subharmonic) followed by receive signal processing.

Conventional medical ultrasound scanners use one-dimensional (1D) arrays containing N transducer elements that may be multiplexed and/or electronically steered and focused via phased array techniques. Usually a half wavelength (LAMBDA/2) spacing is required between elements in order to avoid producing undesirable grating lobes in the array response. This is why a large number of array elements (e.g., N=128) must be employed in realistic imaging systems. Even then, a linear array is limited to focusing and steering only in the array direction.

In recent years, N×M matrix arrays have been introduced on state-of-the-art ultrasound scanners. The multiple (M>1) rows of elements enable electronic focusing in the elevation dimension, thereby producing much improved contrast resolution over an extended axial range. However, the number of rows in these matrix arrays is still quite limited (M<10), and they do not support beam steering in the elevation dimension. For this reason, they are referred to as "1.5D" arrays.

The development of true 2D transducer arrays which allow focusing and beam steering in both lateral dimensions continues to receive much attention because such transducer arrays can potentially enable real-time 3D volumetric imaging, and other advanced imaging techniques, such as phase aberration correction. One of the primary challenges in realizing a 2D array is that the number of beamformer channels (with A/D converters and focusing delays) required becomes prohibitively large. For example, a 64×64 element array requires over 4000 beamformer channels. For this reason, much research effort has been devoted towards development of methods for reducing the number of elements in a 2D array, while maintaining the beam properties similar to those obtained with the full 2D array. As investigated by Turnbull and Foster ("Beam steering with pulsed two-dimensional transducer arrays," IEEE Trans. Ultrasonics, Ferroelectrics, and Frequency Control, Vol. 18, pp. 320–333, 1991), one method is to use a circular rather than a square aperture, which can reduce the element count by about 25%. A more aggressive element reduction scheme, adapted from radar antenna ray theory, is to remove a random selection of elements from the periodic dense array, such that the resultant "sparse array" contains only a small fraction (e.g., 15%) of the original elements. As used herein, the term "sparse array" refers to an array of active transducer elements arranged on a grid comprising a multiplicity of periodically spaced grid points, wherein only a fraction of the grid points are occupied by active transducer elements. The grid points may be arranged in a square, rectangular, hexagonal, triangular or any other suitable geometric pattern. In the case where a transducer element is placed at every grid point, i.e., a so-called "fully populated array", less than all of the elements are activated during either transmit or receive. Alternatively, the sparse array can be formed by forming transducer elements at only the selected grid points making up the sparse array, leaving the remaining grid points unoccupied. The former case is preferred due to the ability to adapt the number and placement of transducer elements by activating a selected subset of elements for a given transmit or receive aperture.

One drawback of sparse arrays is that the large spacing between active elements will invariably give rise to high sidelobes and/or grating lobes which can cause major degradations in image quality. In general, the average sidelobe level will increase with the number of elements removed. To reduce these undesirable effects, a number of sparse array strategies have been proposed which may involve either random or intelligent selection of active elements. The optimal configuration depends on the goodness criteria, such as minimizing the peak sidelobe, minimizing the first sidelobes and minimizing the difference between the response of the actual array and a dense array response. Unfortunately, none of these strategies can keep all sidelobes to within acceptable levels under all scan situations.

There is a need for a method and an apparatus for enhancing the sidelobe performance of a sparse ultrasonic transducer array.

SUMMARY OF THE INVENTION

The present invention is a method and an apparatus for enhancing the sidelobe performance of a sparse ultrasonic transducer array using harmonic imaging to reduce all beam sidelobe (including grating lobe) levels. The invention has applicability to 1D, 1.25D, 1.5D, 1.75D and 2D arrays. As used herein, these terms have the following meanings: 1.25D) elevation aperture is variable, but focusing remains static; 1.5D) elevation aperture, shading, and focusing are dynamically variable, but symmetric about the centerline of the array; 1.75D) elevation geometry and control are similar to 1.5D, but without the symmetry constraint; and 2D) elevation geometry and performance are comparable to azimuth, with full electronic apodization, focusing and steering. The elevation aperture of a 1.25D probe increases with range, but the elevation focusing of that aperture is static and determined principally by a mechanical lens with a fixed focus (or foci). 1.25D probes can provide substantially better near- and far-field slice thickness performance than 1D probes, and require no additional system beamformer channels. 1.5D probes use additional beamformer channels to provide dynamic focusing and apodization in elevation. 1.5D probes can provide detail resolution comparable to, and contrast resolution substantially better than, 1.25D probes, particularly in the mid- and far-field. 1.75D probes, with independent control of the beamforming time delays for all elements in the aperture, allow the beamformer to adaptively compensate for inhomogeneous propagation velocities in the body (or nonuniformities in the imaging system or transducer). In addition to such adaptive beamforming or phase aberration control, 1.75D probes may also support limited beam steering in the elevation direction. By providing at least apodization (1.25D) and perhaps dynamic beamforming (1.5D), phase aberration control (1.75D), or full 2D beam steering, multi-row transducer arrays significantly improve upon the limited elevation performance of 1D probes.

For either a sparse or full transducer array, harmonic imaging consists of using the active transducer elements to transmit an ultrasound signal (wideband or narrowband) of center frequency $f_0$ and receive at one or more harmonic frequencies $nf_0$, where $n \geq 2$. For example, the B-mode image is formed using the signal band centered at $2f_0$ (or higher) versus $f_0$ in conventional imaging.

It has been well established that the transmitted finite-amplitude ultrasound waves undergo nonlinear propagation in tissue such that the waveform becomes progressively distorted and will eventually turn into a shock wave with an abrupt pressure front. In the frequency domain, the progressive waveform distortion means that more and more energy is pumped from the $f_o$ band to the second and higher harmonic frequency bands.

The key to the sidelobe reduction mechanism in harmonic imaging is that the amount of harmonics generated at a given depth can vary with the total pressure amplitude in a highly nonlinear manner, depending on the mechanical properties of the tissue medium. This means that the mainlobe of the beam always tends to generate disproportionately larger harmonics than the sidelobes. Consequently, the second (or higher) harmonic beam profile becomes significantly narrower than that formed by the primary frequency, and with much reduced sidelobe levels. This theory has been recently proven via simulations and experiments based on 1D full arrays, and is taught in detail by Christopher in PCT International Patent Publication No. WO 98/20361, entitled "Finite Amplitude Distortion-Based Inhomogeneous Pulse Echo Ultrasound Imaging".

DETAILED DESCRIPTION OF THE PREFERRED EMBODIMENTS

Figure 1:
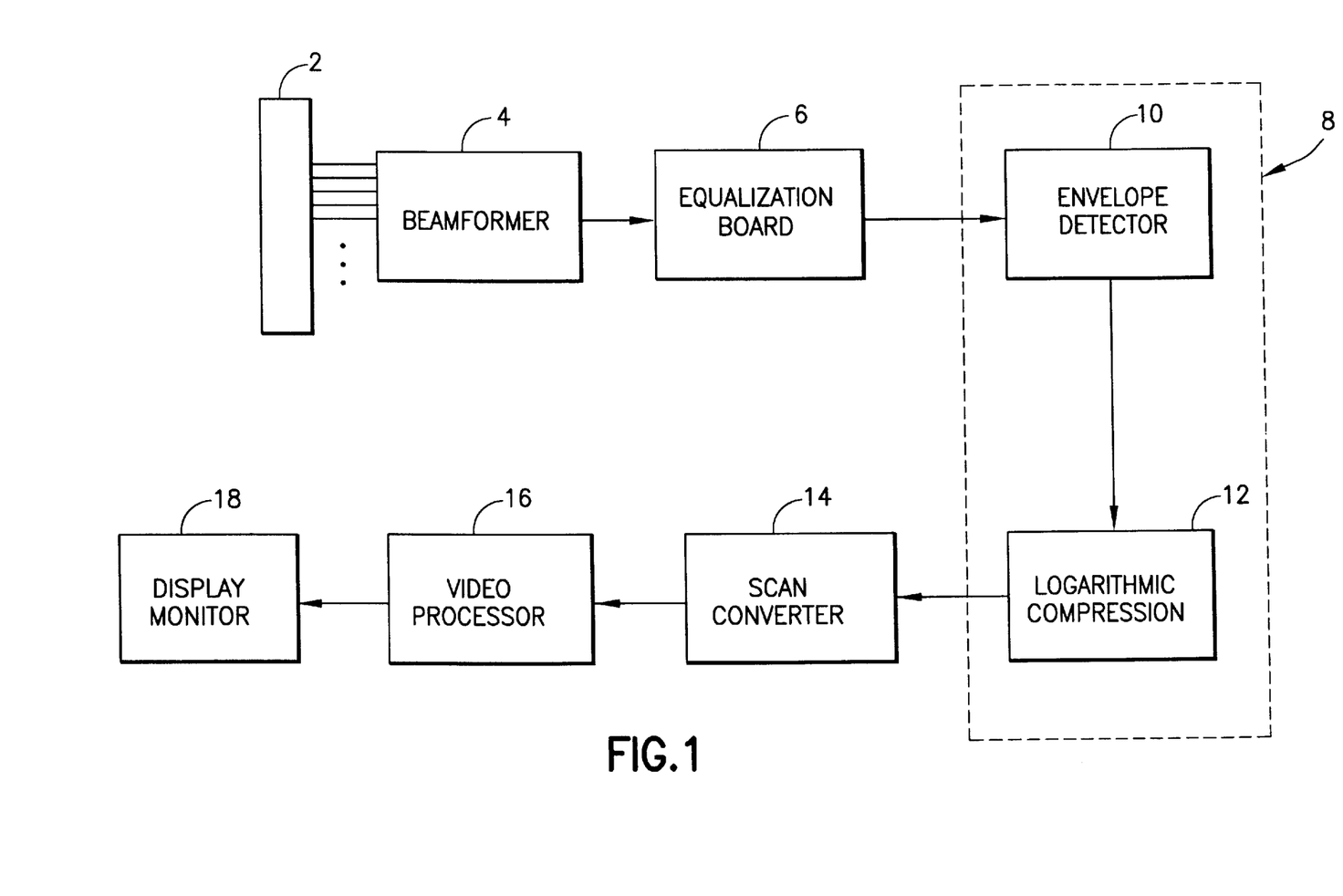
FIG. 1 is a block diagram showing the major functional subsystems within a real-time B-mode ultrasound imaging system.

FIG. 1 shows the functional subsystems of an ultrasound imaging system in which the invention can be incorporated. An ultrasound transducer array 2 is activated to transmit a series of wavelets which are focused at the same transmit focal position with the same transmit characteristics. Each transmit beam propagates through the object being scanned and is reflected by ultrasound scatterers in the object.

After each transmit firing, the echo signals detected by the transducer array elements are fed to respective receive channels of the beamformer 4. The receive beamformer tracks echoes under the direction of a master controller (not shown in FIG. 1). The receive beamformer imparts the proper receive focus time delays to the received echo signal and sums them to provide an echo signal which accurately indicates the total ultrasonic energy reflected from a succession of ranges corresponding to a particular transmit focal position.

The output of the beamformer 4 is then digitally gained, windowed and filtered by circuitry on an equalization board. The filtered beamsummed receive signal is then sent to a B-mode processor 8, which incorporates an envelope detector 10 for forming the envelope of the beamsummed receive signal. The envelope of the signal undergoes some additional B-mode processing, such as logarithmic compression (block 12 in FIG. 1), to form display data which is output to the scan converter 14.

In general, the display data is converted by the scan converter 14 into X-Y format for video display. The scan-converted frames are passed to a video processor 16, which maps the video data to a gray scale or mapping for video display. The gray scale image frames are then sent to the video monitor 18 for display.

The images displayed by the video monitor 18 are produced from an image frame of data in which each datum indicates the intensity or brightness of a respective pixel in the display. An image frame may, e.g., comprise a 256×256 data array in which each intensity datum is an 8-bit binary number that indicates pixel brightness. The brightness of each pixel on the display monitor 18 is continuously refreshed by reading the value of its corresponding element in the data array in a well-known manner. Each pixel has an intensity value which is a function of the backscatter cross section of a respective sample volume in response to interrogating ultrasonic pulses and the gray map employed.

Figure 2:
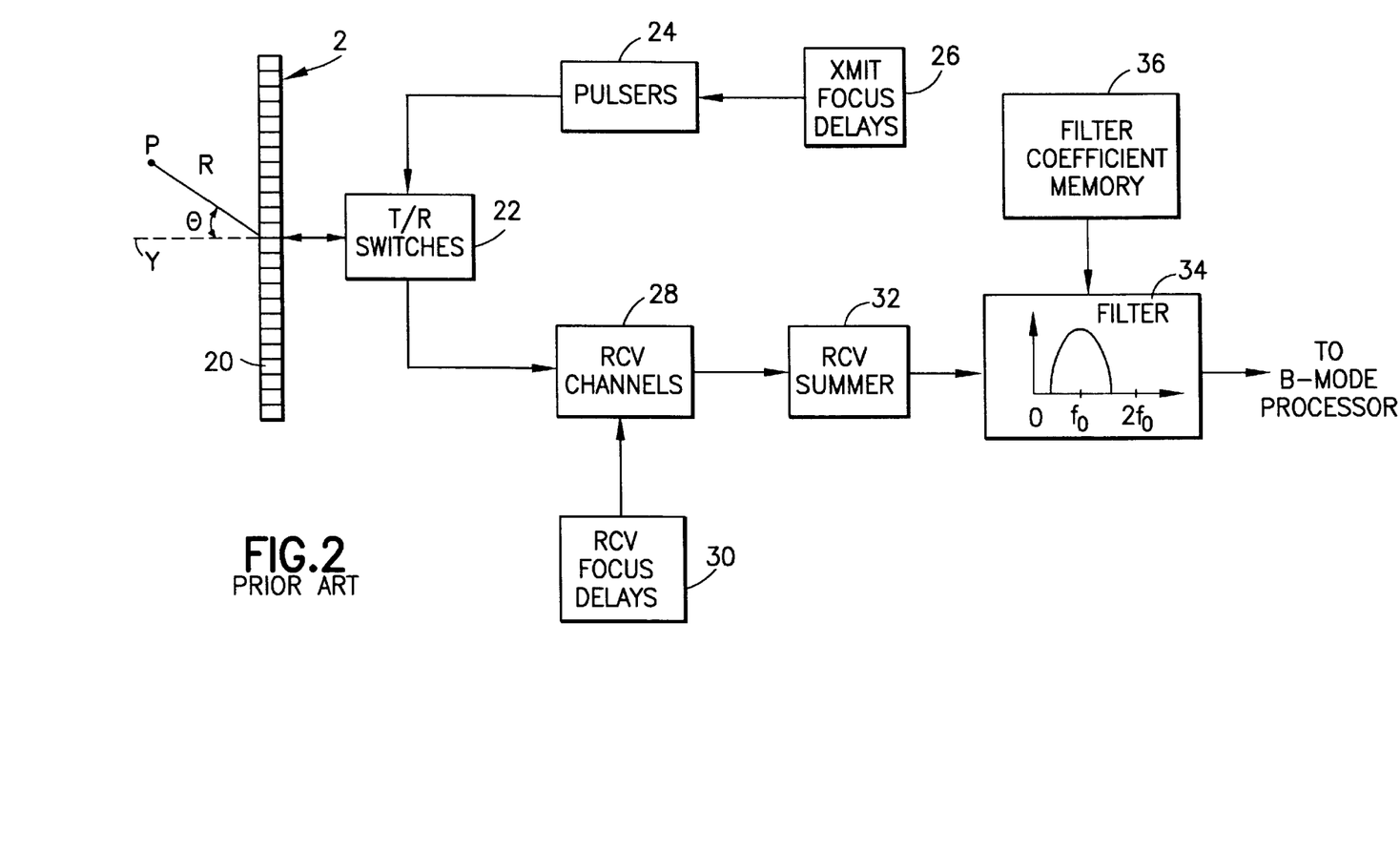
FIG. 2 is a block diagram showing the details of the pulsing and receiving subsystems in the beamformer of a conventional ultrasound scanner with a 1D transducer array.

Referring to FIG. 2, a conventional ultrasonic imaging system incorporates a transducer array 2 comprising a plurality of separately driven transducer elements 20, each of which produces a burst of ultrasonic energy when energized by a pulsed waveform produced by a transmit section of the beamformer 4. The ultrasonic energy reflected back to transducer array 2 from the object under study is converted to an electrical signal by each receiving transducer element 20 and applied separately to a receive section of beamformer 4 through a set of transmit/receive (T/R) switches 22. The T/R switches 22 may be incorporated in multiplexer chips.

The transmit and receive sections of the beamformer are operated under control of a beamformer controller (not shown) responsive to commands by a human operator. The elements of the transducer array 2 are driven such that the ultrasonic energy produced is directed, or steered, in a beam. To accomplish this, respective time delays are imparted to a multiplicity of pulsers 24. Each pulser is connected to a respective transducer element via the T/R switches. The transmit focus time delays are preferably read from a look-up table 26. By appropriately adjusting the transmit focus time delays in a conventional manner, the ultrasonic beam can be directed away from axis Y by an angle θ and/or focused at a fixed range R. A sector scan is performed by progressively changing the transmit focus time delays in successive excitations. The angle θ is thus changed in increments to steer the transmitted beam in a succession of directions.

The echo signals produced by each burst of ultrasonic energy reflect from objects located at successive ranges along the ultrasonic beam. The echo signals are sensed separately by each transducer element 20 and a sample of the magnitude of the echo signal at a particular point in time represents the amount of reflection occurring at a specific range. Due to the differences in the propagation paths between a reflecting point P and each transducer element 20, however, these echo signals will not be detected simultaneously and their amplitudes will not be equal. The receive section of beamformer 4 imparts the proper time delay to each received signal and sums them to provide a single echo signal which accurately indicates the total ultrasonic energy reflected from point P located at range R along the ultrasonic beam oriented at the angle θ. To accomplish this, respective receive focus time delays are imparted to a multiplicity of receive channels 28. Each receive channel is connected to a respective transducer element via a T/R switch. The receive focus time delays are preferably read from a look-up table 30. The receive channels also have circuitry (not shown) for apodizing and filtering the received pulses. The time-delayed receive signals are then summed in receive summer 32. The summed signal is then bandpass filtered by an equalization filter 34 on the equalization board which is programmed, using a first set of filter coefficients, to pass a band of frequencies centered at the fundamental frequency $f_0$. The filter response is depicted inside the block labeled 34. The filter 34 is preferably an FIR filter having M filter taps for receiving a set of M filter coefficients from a filter coefficient memory 36. The filter coefficients, like the transmit and receive time delays, can be supplied by the master controller (not shown). Filter 34 outputs the filtered signal to the B-mode processor 8 (see FIG. 1).

Figure 3:
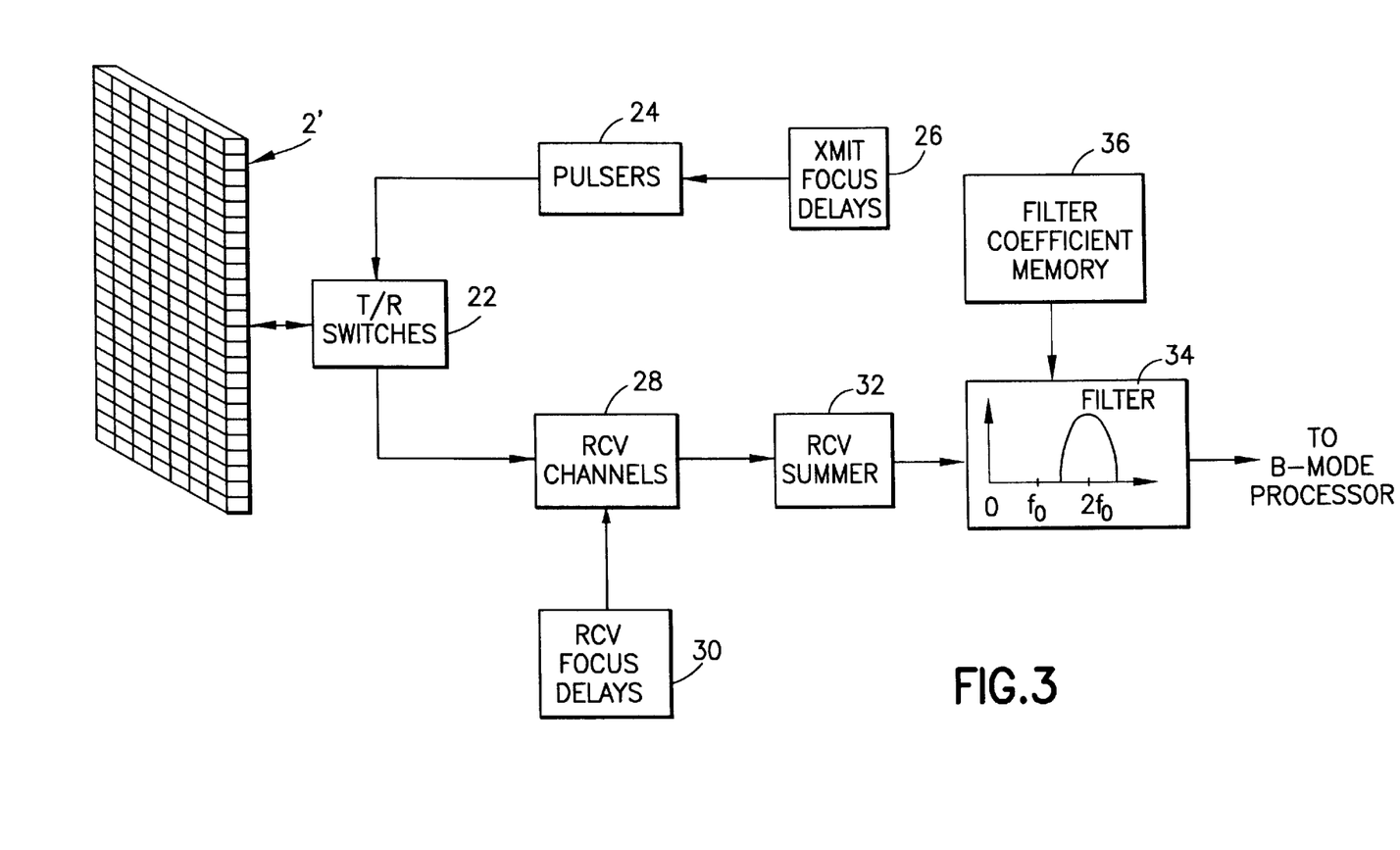
FIG. 3 is a block diagram showing the use of an N×M array in conjunction with harmonic imaging in accordance with the invention. In this illustration, the second harmonic frequency band is selected by the filter for B-mode image processing.

In accordance with the preferred embodiment of the invention shown in FIG. 3, an array 2' of transducer elements is arranged in rows and columns, thus forming a grid of elements. To form a sparse array, only a fraction of the elements are activated on transmit and on receive. The same elements need not be activated during both transmit and receive. Which elements are activated is determined by the setting of the T/R switches 22, which are preferably multiplexer switches controlled by a master controller (not shown in FIG. 3). During transmit, the pulsers drive the transducer elements to transmit wavelets at the fundamental frequency $f_0$. The equalization filter 34 is programmed, using a second set of filter coefficients retrieved from the filter coefficient memory 36, to pass a band of frequencies centered at a harmonic frequency, e.g., $2f_0$. The filter response in this case is again depicted inside the block labeled 34. Filter 34 then outputs the raw harmonic frequency data to the B-mode processor for envelope detection. The imaging of harmonic frequency data instead of the fundamental frequency data enhances the sidelobe performance of the sparsely configured ultrasonic transducer array by reducing all beam sidelobe (including grating lobe) levels.

Figure 4:
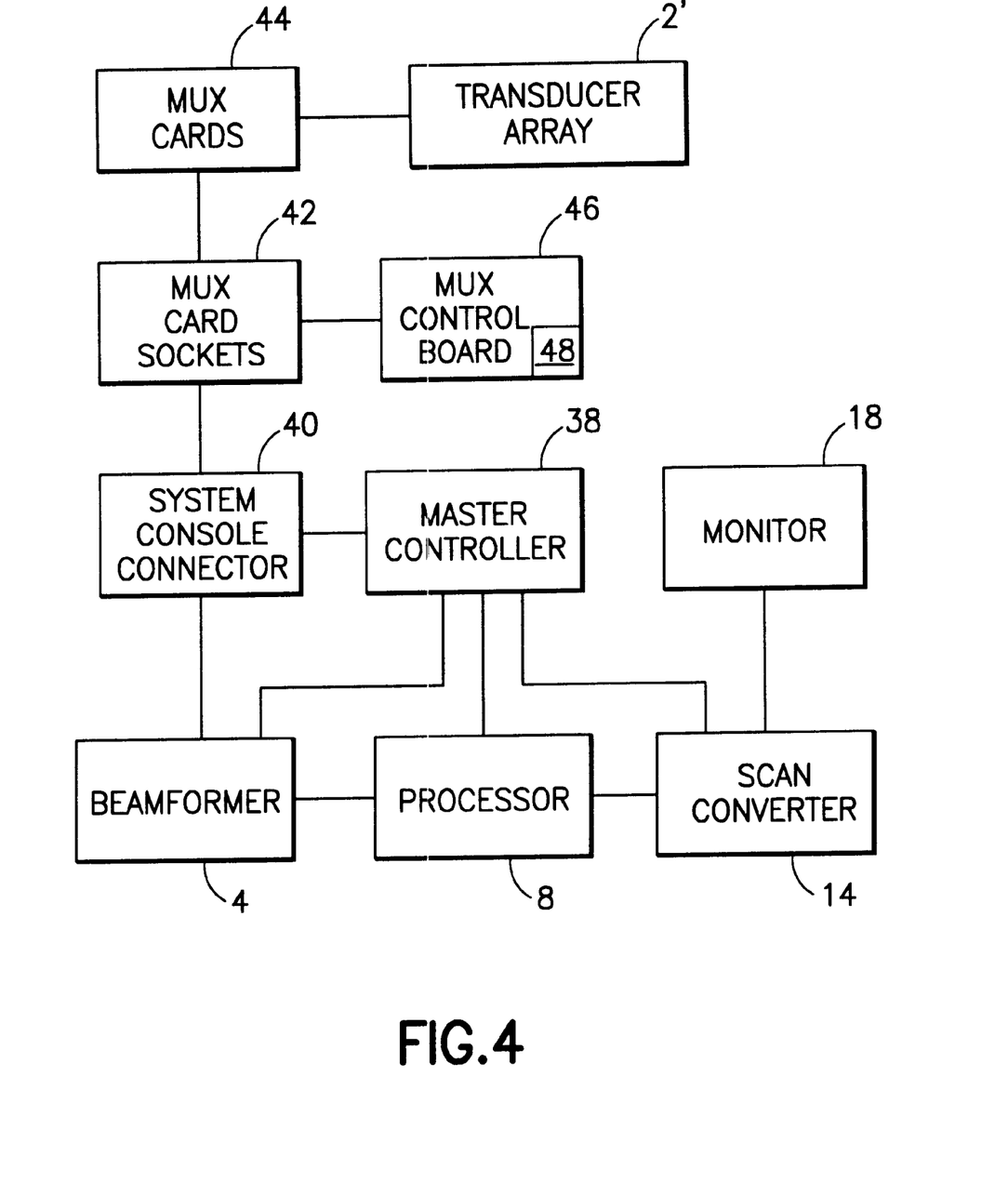
FIG. 4 is a block diagram showing part of an ultrasound imaging system incorporating a modular multiplexer in accordance with a preferred embodiment of the invention.

One preferred embodiment of the invention which incorporates a multiplexer for connecting the sparse array to the beamformer is shown in FIG. 4. The elements of transducer array 2' are connected to the channels of beamformer 4 via a system console connector 40. The multiplexer is controlled by a parameter called MUX State, which is transmitted by the master controller 38 to control lines on the system console connector 40. The MUX State parameter is generated in accordance with a transducer multiplexer control program stored in the master controller. In the case where the sparse array used on transmit differs from the sparse array used on receive, separate MUX State parameters are provided for transmit and receive. The multiplexer backplane or motherboard (not shown) mounts on the system console connector 40. The backplane contains identical sockets 42 for multiplexer cards 44. The multiplexer control board 46 is connected to control lines on the console connector 40 and separate (not paralleled) control lines to each multiplexer card socket 42. The control board 46 receives a concise MUX State command from the master controller 38 and uses data stored in on-board memory 48 (ROM or EEPROM) to set every switch on every multiplexer card 44 to the open or closed position required for the commanded multiplexer state.

While the novel concept of combining a sparse array and harmonic imaging is shown in FIGS. 3 and 4, it should be obvious to those skilled in the art that a wide range and mix of specific implementations are possible in practice. For instance, it will be readily appreciated that a 1D sparse array can be linear or curvilinear. For a 2D array, the aperture can be flat, concave or convex, and it does not have to be rectangular or square or even symmetric in shape. Furthermore, the element distribution of the transducer array may vary with the transmit focus position. It may well start out to be a full (or dense) but small aperture in the near field when the total element count can be supported by the beamformer channels. As the aperture opens up for the deeper focal zones, and the beamformer can no longer support a full aperture, the sparse array strategy can then be engaged. Optionally, the element distribution in a sparse array can be different between the transmit and receive apertures. This is important for designing an optimal two-way beam profile which is given by the product of the transmit and receive beam profiles. For either the transmit or receive aperture, the element distribution may assume a design pattern depending on the desired beam profile response. An example of a symmetric element distribution pattern for a 2D sparse array is shown in FIG. 3a of a paper by Smith et al. ("Two-dimensional arrays for medical ultrasound," Ultrasonic Imaging, Vol. 14, pp. 213–233, 1992). Alternatively, the element distribution may take on a random pattern such as that shown in FIG. 10a of the Turnbull and Foster paper cited above. Also, harmonic imaging is not restricted to the second harmonic frequency band: provided that the transducer array and equalization filter have sufficiently large bandwidth, higher harmonic frequency bands can be used. On state-of-the-art imagers in which two parallel equalization filters and B-mode detectors (left and right) are available, the left and right equalization filters can be set independently to pass the fundamental and harmonic frequency bands, respectively. This would enable a mix of primary and secondary (or higher) harmonic frequency components to be summed after detection to form a compounded B-mode image. Both the center frequency and bandwidth of the equalization filters can be adjusted dynamically with time (range). In the near-field, more primary frequency component can be used if the harmonics generated in tissue are not very strong yet. In the mid-field, more second harmonic component can be used to suppress the sidelobes associated with the sparse array. Some primary component may be included to increase the signal-to-noise ratio, and very good overall sidelobe suppression is still possible because the sidelobes of the second harmonic beam are somewhat chaotic and often destructively interfere with those of the primary beam. In the far-field, tissue absorption effects become dominant so that the image is now limited by system noise and not by sparse array beam sidelobe artifacts; in that situation it may make sense to use more primary frequency component again to form the B-mode image. The relative amounts of primary and secondary frequency components can be varied by applying respective weighting factors to the equalization filters prior to summation or by adjusting the filter coefficients to vary the respective gains of the equalization filters.

The foregoing preferred embodiments have been disclosed for the purpose of illustration. Variations and modifications which fall within the broad concept of the invention will be readily apparent to those skilled in the art. While the present invention is intended primarily to enhance sparse array B-mode imaging by utilizing the nonlinear-propagation-induced harmonic signals in tissue, it can also be applied to contrast-agent enhanced color flow imaging. In the latter case, the harmonic signals are generated due to nonlinear oscillations of the contrast agents in blood. All such variations and modifications are intended to be encompassed by the claims set forth hereinafter.

I claim:

1. A system for imaging of ultrasound scatterers, comprising:
    an ultrasound transducer array comprising a multiplicity of elements and having a transmit aperture and a receive aperture, said transmit and receive apertures being formed by respective configurations of said elements, at least said configuration of said receive aperture being sparse;
    a transmit beamformer for pulsing the transducer elements making up said transmit aperture with wavelets having a fundamental frequency $f_0$ during a transmit firing;
    a receive beamformer coupled to the transducer elements making up said receive aperture of said transducer array for acquiring a beamsummed signal subsequent to said transmit firing;
    a filter for passing a harmonic frequency component of said beamsummed signal having a frequency substantially equal to $nf_0$, where n is a positive integer $\geq 2$;
    a processor programmed to form an image signal from said harmonic frequency component of said beamsummed signal; and
    means for displaying an image which is a function of said image signal.

2. The system as defined in claim 1, wherein said filter is a bandpass filter which passes a band of frequencies centered at said harmonic frequency substantially equal to $nf_0$.

3. The system as defined in claim 1, wherein said configuration of said transmit aperture is sparse.

4. A system for imaging of ultrasound scatterers, comprising:
    an ultrasound transducer array comprising a multiplicity of elements and having a first transmit aperture and a first receive aperture for a first transmit focal position and a second transmit aperture and a second receive aperture for a second transmit focal position, said first transmit and first receive apertures being formed by respective dense configurations of said elements, and said second transmit and second receive apertures being formed by respective configurations of said elements, at least said configuration of said second receive aperture being sparse, said first and second transmit focal positions having different ranges;
    a transmit beamformer for pulsing the transducer elements making up said first and second transmit apertures with wavelets having a fundamental frequency $f_0$ during first and second transmit firings respectively;
    a receive beamformer coupled to the transducer elements making up said first receive aperture of said transducer array for acquiring a first beamsummed signal subsequent to said first transmit firing and coupled to the transducer elements making up said second receive aperture of said transducer array for acquiring a second beamsummed signal subsequent to said second transmit firing;
    a first filter for passing a fundamental frequency component of said first beamsummed signal having a frequency substantially equal to $f_0$;
    a second filter for passing a harmonic frequency component of said second beamsummed signal having a frequency substantially equal to $nf_0$, where n is a positive integer greater than or equal to 2;
    a processor programmed to form a first image signal rom said fundamental frequency component of said first beamsummed signal and a second image signal from said harmonic frequency component of said beamsummed signal;
    means for combining said first and second image signals to form a combined image signal; and
    means for displaying an image which is a function of said combined image signal.

5. The system as defined in claim 4, further comprising means for storing first and second sets of filter coefficients, means for programming said first filter with said first set of filter coefficients to pass said fundamental frequency component and means for programming said second filter with said second set of filter coefficients to pass said harmonic frequency component.

6. The system as defined in claim 4, wherein said configuration of said second transmit aperture is sparse.

7. The system as defined in claim 4, further comprising means for dynamically adjusting a center frequency and a bandwidth of at least one of said first and second filters as a function of range.

8. A system for imaging of ultrasound scatterers, comprising:
    an ultrasound transducer array comprising a multiplicity of elements and having a first transmit aperture and a first receive aperture for a first transmit focal position along a beam and a second transmit aperture and a second receive aperture for a second transmit focal position along said beam, said first transmit and first receive apertures being formed by respective dense configurations of said elements, said second transmit and second receive apertures being formed by respective configurations of said elements, at least said configuration of said second receive aperture being sparse, said first and second transmit focal positions along said beam having different ranges;

a transmit beamformer for pulsing the transducer elements making up said first and second transmit apertures with wavelets having a fundamental frequency during first and second transmit firings respectively;

a receive beamformer coupled to the transducer elements making up said first receive aperture of said transducer array for acquiring a first beamsummed signal subsequent to said first transmit firing and coupled to the transducer elements making up said second receive aperture of said transducer array for acquiring a second beamsummed signal subsequent to said second transmit firing;

a first filter for passing a fundamental frequency component having a frequency substantially equal to $f_0$, said first filter being coupled to receive said first and second beamsummed signals;

a second filter for passing a harmonic frequency component having a frequency substantially equal to $nf_0$, where n is a positive integer greater than or equal to 2, said second filter being coupled to receive said first and second beamsummed signals;

means for adjusting the relative amplitudes of said first and second filter outputs in accordance with a first weighting for said first beamsummed signal and in accordance with a second weighting different than said first weighting for said second beamsummed signal;

a processor programmed to form a first image signal from said weighted first and second filter outputs for said first beamsummed signal and a second image signal from said weighted first and second filter outputs for said second beamsummed signal; and means for displaying an image having a first image portion which is a function of said first image signal and a second image portion which is a function of said second image signal.

9. A system for imaging of ultrasound scatterers, comprising:

a sparse ultrasound transducer array comprising a multiplicity of elements and having a transmit aperture and a receive aperture;

a transmit beamformer for pulsing the transducer elements making up said transmit aperture with wavelets having a fundamental frequency f during a transmit firing;

a receive beamformer coupled to the transducer elements making up said receive aperture of said transducer array for acquiring a beamsummed signal subsequent to said transmit firing;

a filter for passing a harmonic frequency component of said beamsummed signal having a frequency substantially equal to $nf_0$, where n is a positive integer $\geq 2$;

a processor programmed to form an image signal from said harmonic frequency component of said beamsummed signal; and means for displaying an image which is a function of said image signal.

10. A method for imaging ultrasound scatterers, comprising the steps of:

driving transducer elements making up a transmit aperture of a transducer array having a first configuration with wavelets having a fundamental frequency f to form a beam;

receiving a set of echo signals from transducer elements making up a receive aperture of said transducer array having a second configuration, wherein at least said second configuration is sparse;

forming a beamsummed receive signal derived from said set of echo signals;

filtering out frequency components of said beamsummed signal not having a frequency lying within a predetermined frequency band substantially centered at a frequency equal to $nf_0$, where n is a positive integer greater than or equal to 2;

processing the frequency components in said predetermined frequency band to form an image signal; and displaying an image which is a function of said image signal.

11. The method as defined in claim 10, wherein said first configuration is sparse.

12. A method for imaging ultrasound scatterers, comprising the steps of:

driving transducer elements making up a transmit aperture of a transducer array having a first configuration with wavelets having a fundamental frequency f to form a beam;

receiving a set of echo signals from transducer elements making up a receive aperture of said transducer array having a second configuration, wherein at least said second configuration is sparse;

forming a beamsummed receive signal derived from said set of echo signals;

forming a first filtered signal by filtering out frequency components of said beamsummed signal not having a frequency lying within a first frequency band substantially centered at a frequency equal to $nf_0$, where n is a positive integer greater than or equal to 2;

forming a second filtered signal by filtering out frequency components of said beamsummed signal not having a frequency lying within a second frequency band substantially centered at a frequency equal to $f_0$;

processing said first and second filtered signals to form first and second image signals respectively;

summing said first and second image signals to form a combined image signal; and displaying an image which is a function of said combined image signal.

13. The method as defined in claim 12, wherein said forming steps comprise the steps of adjusting the relative amplitudes of said first and second filtered signals.

14. The method as defined in claim 12, wherein said summing step comprises the step of weighting said first and second image signals before summing.

15. The method as defined in claim 12, wherein said first configuration is sparse.

16. A system for imaging of ultrasound scatterers, comprising:

a sparse ultrasound transducer array comprising a multiplicity of elements and having a transmit aperture and a receive aperture;

a transmit beamformer for pulsing the transducer elements making up said transmit aperture with wavelets having a fundamental frequency f during a transmit firing;

a receive beamformer coupled to the transducer elements making up said receive aperture of said transducer array for acquiring a beamsummed signal subsequent to said transmit firing;

a filter for passing a harmonic frequency component comprising a band of frequencies of said beamsummed signal substantially centered at a frequency $nf_0$, where n is a positive integer greater than or equal to 2;

a processor programmed to form an image signal from said harmonic frequency component of said beamsummed signal; and means for displaying an image which is a function of said image signal.

17. A system for imaging of ultrasound scatterers, comprising an ultrasound transducer array, a display monitor and a data processor programmed to perform the following steps:

driving transducer elements making up a transmit aperture of said transducer array having a first configuration with wavelets having a fundamental frequency f to form a beam;

receiving a set of echo signals from transducer elements making up a receive aperture of said transducer array having a second configuration, wherein at least said second configuration is sparse;

forming a beamsummed receive signal derived from said set of echo signals;

filtering out frequency components of said beamsummed signal not having a frequency lying within a predetermined frequency band substantially centered at a frequency equal to $nf_0$, where n is a positive integer greater than or equal to 2;

processing the frequency components in said predetermined frequency band to form an image signal; and displaying a first image frame which is a function of said image signal on said display monitor.

18. A system for imaging of ultrasound scatterers, comprising an ultrasound transducer array, a display monitor and a data processor programmed to perform the following steps:

driving transducer elements making up a transmit aperture of said transducer array having a first configuration with wavelets having a fundamental frequency f to form a beam;

receiving a set of echo signals from transducer elements making up a receive aperture of said transducer array having a second configuration, wherein at least said second configuration is sparse;

forming a beamsummed receive signal derived from said set of echo signals;

forming a first filtered signal by filtering out frequency components of said beamsummed signal not having a frequency lying within a first frequency band substantially centered at a frequency equal to $nf_0$, where n is a positive integer greater than or equal to 2;

forming a second filtered signal by filtering out frequency components of said beamsummed signal not having a frequency lying within a second frequency band substantially centered at a frequency equal to $f_o$;

processing said first and second filtered signals to form first and second image signals respectively;

summing said first and second image signals to form a combined image signal; and displaying an image which is a function of said combined image signal on said display monitor.

19. A system for imaging of ultrasound scatterers, comprising:

an ultrasound transducer array comprising a multiplicity of transducer elements;

a display monitor;

means for driving transducer elements making up a transmit aperture of said transducer array having a first configuration with wavelets having a fundamental frequency f to form a beam;

means for receiving a set of echo signals from transducer elements making up a receive aperture of said transducer array having a second configuration, wherein at least said second configuration is sparse;

means for forming a beamsummed receive signal derived from said set of echo signals;

means for filtering out frequency components of said beamsummed signal not having a frequency lying within a predetermined frequency band substantially centered at a frequency equal to $nf_0$, where n is a positive integer greater than or equal to 2;

means for processing the frequency components in said predetermined frequency band to form an image signal; and means displaying a first image frame which is a function of said image signal on said display monitor.

20. A system for imaging of ultrasound scatterers, comprising:

an ultrasound transducer array comprising a multiplicity of transducer elements;

a display monitor;

means for driving transducer elements making up a transmit aperture of said transducer array having a first configuration with wavelets having a fundamental frequency f to form a beam;

means for receiving a set of echo signals from transducer elements making up a receive aperture of said transducer array having a second configuration, wherein at least said second configuration is sparse;

means for forming a beamsummed receive signal derived from said set of echo signals;

means for filtering out frequency components of said beamsummed signal not having a frequency lying within a first frequency band substantially centered at a frequency equal to nf to form a first filtered signal, where n is a positive integer greater than or equal to 2;

means for filtering out frequency components of said beamsummed signal not having a frequency lying within a second frequency band substantially centered at a frequency equal to f to form a second filtered signal;

means for processing said first and second filtered signals to form first and second image signals respectively;

means for summing said first and second image signals to form a combined image signal; and means for displaying an image which is a function of said combined image signal on said display monitor.

* * * * *